(12) United States Patent
Morse et al.

(10) Patent No.: US 10,350,049 B2
(45) Date of Patent: Jul. 16, 2019

(54) LAMINATED TISSUE GRAFTS COMPOSED OF WHARTON'S JELLY AND METHODS OF MAKING AND USING THE SAME

(75) Inventors: Brenda S. Morse, Marietta, GA (US); Somaly Sith, Marietta, GA (US); Randall Spencer, Marietta, GA (US); John Daniel, Marietta, GA (US); Robert Tofe, Denver, CO (US)

(73) Assignee: MiMedx Group, Inc., Marietta, GA (US)

( * ) Notice: Subject to any disclaimer, the term of this patent is extended or adjusted under 35 U.S.C. 154(b) by 231 days.

(21) Appl. No.: 13/984,843

(22) PCT Filed: Feb. 13, 2012

(86) PCT No.: PCT/US2012/024858
§ 371 (c)(1),
(2), (4) Date: Aug. 6, 2014

(87) PCT Pub. No.: WO2012/112441
PCT Pub. Date: Aug. 23, 2012

(65) Prior Publication Data
US 2014/0343688 A1    Nov. 20, 2014

Related U.S. Application Data

(60) Provisional application No. 61/442,343, filed on Feb. 14, 2011.

(51) Int. Cl.
*A61L 27/36* (2006.01)
*A61L 27/50* (2006.01)
*A61F 2/02* (2006.01)

(52) U.S. Cl.
CPC ............ *A61F 2/02* (2013.01); *A61L 27/3604* (2013.01); *A61L 27/3683* (2013.01); *A61L 27/50* (2013.01); *A61L 2430/40* (2013.01)

(58) Field of Classification Search
CPC .................................................... A61K 35/50
See application file for complete search history.

(56) References Cited

U.S. PATENT DOCUMENTS

| | | |
|---|---|---|
| 2009/0033160 A1 | 2/2009 | Mueller |
| 2010/0098743 A1 | 4/2010 | Nikaido et al. |
| 2010/0104539 A1 | 4/2010 | Daniel et al. |
| 2010/0222253 A1 | 9/2010 | Roedersheimer |
| 2011/0256202 A1 | 10/2011 | Tom et al. |

FOREIGN PATENT DOCUMENTS

| | | | |
|---|---|---|---|
| WO | WO 93/10722 | * 6/1993 | ............... A61F 2/02 |
| WO | WO-2009/033160 A1 | 3/2009 | |
| WO | WO-2009/132186 A1 | 10/2009 | |

OTHER PUBLICATIONS

Jeschke et al, The Open Tissue Engineering and Regenerative Medicine Journal, 2011, vol. 4, pp. 21-27.*
Final Written Decision in Case IPR2015-00664, issued by PTAB dated Aug. 16, 2016. (Year: 2016).*
EP Search Report for European Patent Application No. 12747175.3 dated Jun. 2, 2015.
Office Action for European Application No. 12474175.3 dated Nov. 15, 2018.
Office Action for Korean Application No. 10-2013-7023863 dated Dec. 12, 2018.
International Search Report and Written Opinion for PCT Patent Application No. PCT/US2012/024858, dated May 30, 2012.
International Preliminary Report on Patentability dated Feb. 19, 2013 in related PCT Patent Application No. PCT/US2012/024858.

* cited by examiner

*Primary Examiner* — Allison M Fox
(74) *Attorney, Agent, or Firm* — Alston & Bird LLP

(57) ABSTRACT

Described herein are tissue grafts derived from the placenta with improved physical and biological properties. In one aspect, the tissue graft includes a first membrane comprising Wharton's jelly laminated with amnion, chorion, or a combination thereof. The presence of Wharton's jelly in the grafts enhances the performance of allograft amniotic-derived, caderivic allograft, xenograft, or alloplast soft tissue substitutes.

18 Claims, 7 Drawing Sheets

LAMINATED TISSUE GRAFTS COMPOSED OF WHARTON'S JELLY AND METHODS OF MAKING AND USING THE SAME

CROSS REFERENCE TO RELATED APPLICATIONS

This application is a 0 371 National Stage entry of P.C.T. International Application No. PCT/US2012/024858, filed Feb. 13, 2012, which claims priority upon U.S. provisional application Ser. No. 61/442,343, filed Feb. 14, 2011. These applications are hereby incorporated by reference in their entireties for all of their teachings.

BACKGROUND

Human placental membrane (e.g. amniotic membrane) has been used for various types of reconstructive surgical procedures since the early 1900s. The membrane serves as a substrate material, more commonly referred to as a biological dressing or patch graft. Such a membrane has also been used widely for ophthalmic procedures and more recently for dental regenerative procedures, treating ulcers and as adhesion barrier. Typically, the membrane is either frozen or dried for preservation and storage until needed for surgery.

Placental tissue is typically harvested after an elective Cesarean surgery. The placenta is composed of the umbilical cord and amniotic sac. The amniotic sac, commonly referred to as the amniotic membrane, has two primary layers of tissue, amnion and chorion. Amnion tissue is the innermost layer of the amniotic sac and in direct contact with the amniotic fluid. The amniotic sac contains the amniotic fluid and protects the fetal environment. Histological evaluation indicates that the membrane layers of the amnion consist of single layer of epithelium cells, thin reticular fibers (basement membrane), a thick compact layer, and fibroblast layer. The fibrous layer of amnion (i.e., the basement membrane) contains collagen types IV, V, and VII, and cell-adhesion bio-active factors including fibronectin and laminins.

SUMMARY

Described herein are tissue grafts derived from the placenta with improved physical and biological properties. In one aspect, the tissue graft includes a first membrane comprising Wharton's jelly laminated with amnion, chorion, or a combination thereof. The presence of Wharton's jelly in the grafts enhances the performance of allograft amniotic-derived, caderivic allograft, xenograft, or alloplast soft tissue substitutes. Methods for making and using the tissue grafts are described herein as well. The advantages of the invention will be set forth in part in the description which follows, and in part will be obvious from the description, or may be learned by practice of the aspects described below. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "amnion stromal layer" is defined herein as the part of the amnion composed of the basement membrane, compact layer, fibroblast layer, and intermediate layer.

The term "amnion" as used herein includes amniotic membrane where the intermediate tissue layer is intact or has been substantially removed.

Titles or subtitles may be used in the specification for the convenience of a reader, which are not intended to influence the scope of the present invention. Additionally, some terms used in this specification are more specifically defined below.

I. Tissue Grafts and Methods for Making Thereof

Described herein are tissue grafts and methods of making and using thereof. In general, the multilayer grafts are composed of a layer of Wharton's jelly laminated with amnion, chorion, or a combination thereof.

Figure 1:
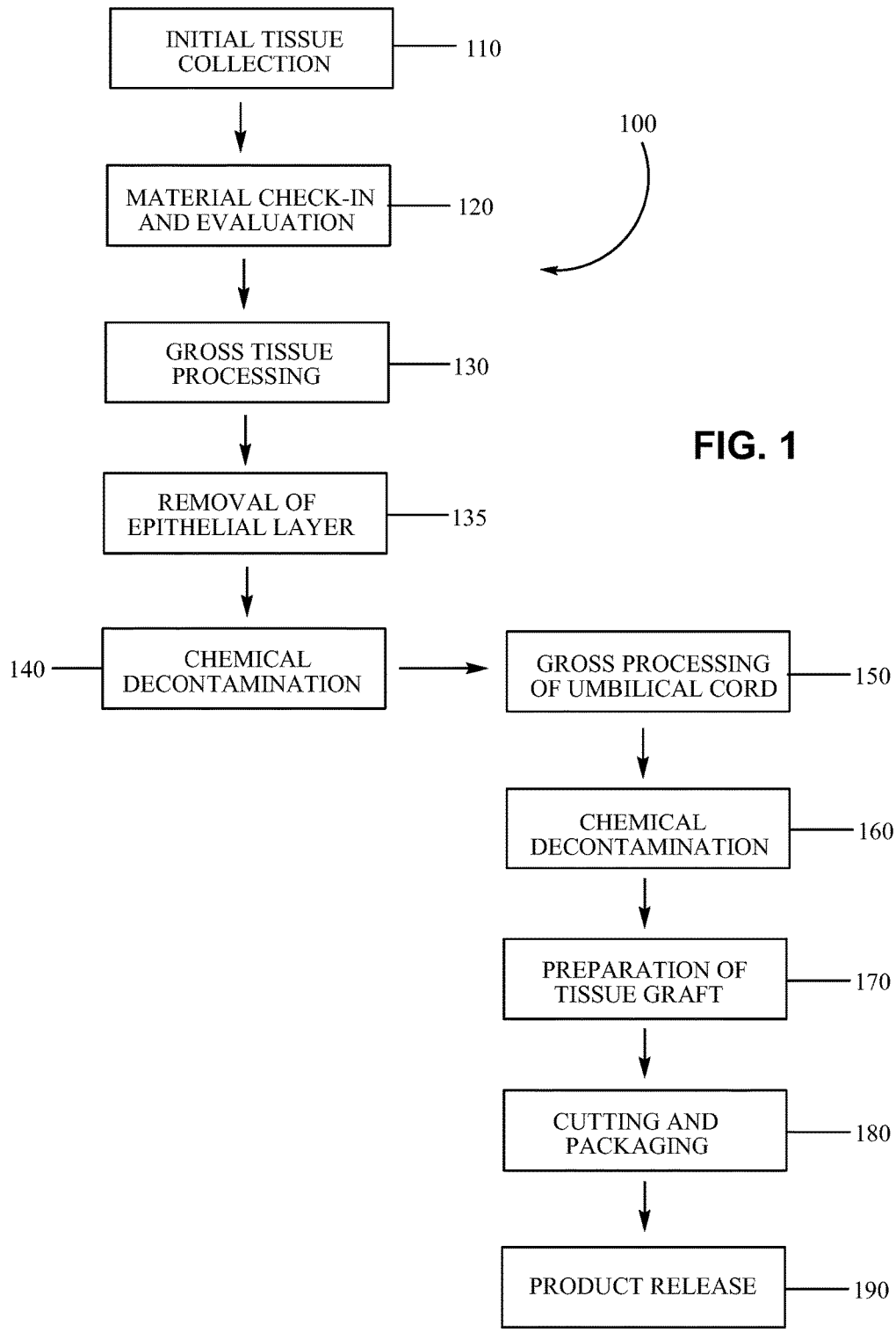
FIG. 1 is an overview flow chart of the process for making the tissue grafts described herein.

FIG. 1 depicts an exemplary overview (100) of the steps to harvest, process, and prepare placental material for later use as a tissue graft. More detailed descriptions and discussion regarding each individual step will follow. Initially, the placenta tissue is collected from a consenting patient following an elective Cesarean surgery (step 110). The material is preserved and transported in a conventional tissue preservation manner to a suitable processing location or facility for check-in and evaluation (step 120). Gross processing, handling, and separation of the amnion and chorion tissue layers then takes place (step 130). After the epithelium layer is substantially removed from the amnion to expose the base membrane (step 135), acceptable tissue is then decontaminated (step 140). Gross processing of the umbilical cord is performed, separating the Wharton's jelly from the umbilical cord vascular components and cutting off the amnion (Step 150). After cutting Wharton's jelly, acceptable tissue is then decontaminated (Step 160). After layering, the graft composed of Wharton's jelly laminated with chorion and/or amnion is dehydrated (step 170), cut into strips, and packaged (step 180). Finally, the graft is radiologically terminally sterilized using electron beam or gamma radiation and released (step 190) to the market for use by surgeons and other medical professionals in appropriate surgical procedures and for wound care. Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing of Amniotic Sac (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below.

Removal of Epithelium Layer from Amnion (Step 135)

The epithelium layer present on the amnion is substantially removed in order to expose the basement layer of the amnion. The significance of removing the epithelium layer is described below. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells. Not wishing to be bound by theory, laminin and laminin-5 are primarily found in the basement membrane; therefore, removal of the epithelium cells from the amnion exposes the basement membrane significantly enhancing the ability of the amnion to release laminin and laminin-5. These glycoproteins are important with respect to the ability of the grafts described herein to mediate the attachment, migration, and organization of cells.

The methods described herein, particularly steps 130 and 135, do not remove all cellular components in the amnion. This technique is referred to in the art as "decellularization." Decellularization generally involves the physical and/or chemical removal of all cells present in the amnion, which includes epithelial cells and fibroblast cells. Although step 135 does remove epithelial cells, the fibroblast layer present in the amnion is intact, even after removal of the intermediate layer discussed in step 130. This is an important distinction, as the removal of the fibroblast reduces the ability of the tissue graft to release components such as proteins and growth factors which plays a critical role in wound healing.

Chemical Decontamination (Step 140)

The amnion and chorion isolated above can be chemically decontaminated using the techniques described below. In one aspect, the amnion and chorion is decontaminated at room temperature. In one aspect, the amnion produced in steps 130 or 135 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate or incubator such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Gross Processing of the Umbilical Cord (Step 150)

Figure 2:
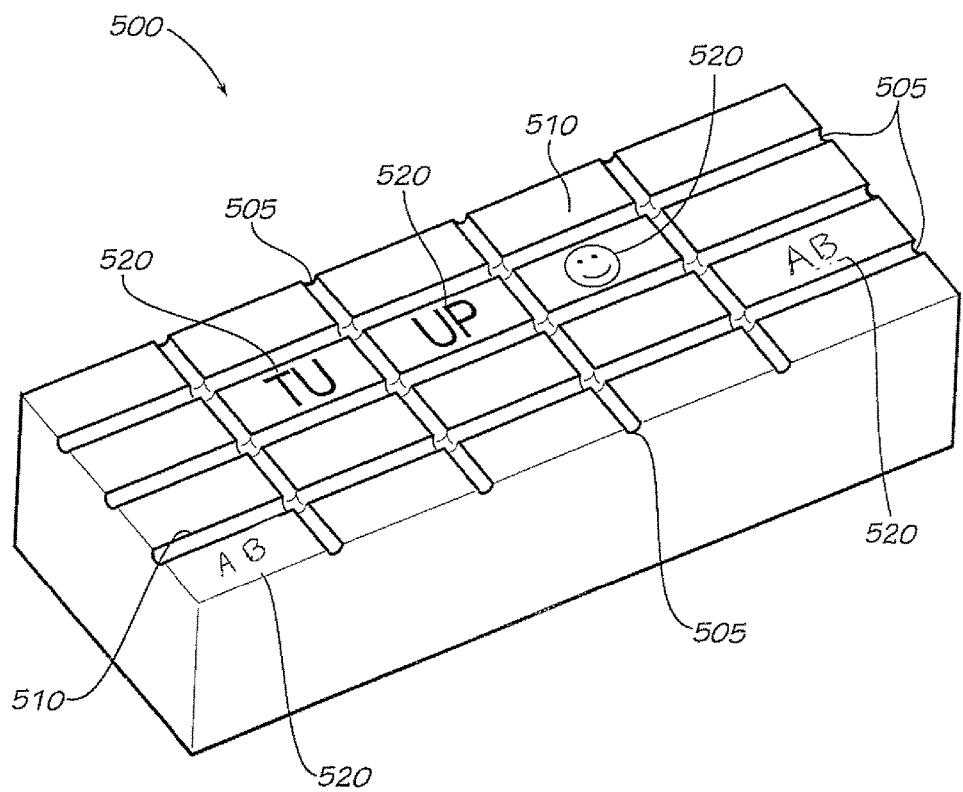
FIG. 2 indicates the location of the incisions in the umbilical cord to facilitate vessel removal and isolation of Wharton's jelly.

Using a scalpel or scissors, the umbilical cord is dissected away from the chorionic disk. Once the veins and the artery have been identified, the cord is dissected lengthwise down one of the veins or the artery, as shown in FIG. 2. Once the umbilical cord has been dissected, surgical scissors and forceps can be used to dissect the vein and artery walls from the Wharton's jelly. Next, the outer layer of amnion is removed from the Wharton's jelly by cutting the amnion. Here, the outer membrane of the umbilical cord is removed such that Wharton's jelly is the only remaining component. Thus, the Wharton's jelly as used herein does not include the outer umbilical cord membrane and umbilical cord vessels. The Wharton's jelly can be cut into strips. In one aspect, the strips are approximately 1-4 cm by 10-30 cm with an approximate thickness of 1.25 cm; however, other thicknesses are possible depending on the application.

Chemical Decontamination (Step 160)

The Wharton's jelly is transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) with 18% NaCl. The container is sealed and placed on rocker plate and agitated for 60 to 90 minutes.

After the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours.

The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After incubation, the jar is returned to the sterile field. The Wharton's jelly should have a cream white visual appearance with no evidence of brownish discoloration.

Preparation of Tissue Graft and Dehydration (Step 170)

The tissue grafts described herein are composed of Wharton's jelly laminated with amnion and/or chorion. The tissue grafts can be composed of a plurality (i.e., greater than two) amnion and chorion membranes laminated to the Wharton's jelly. For example, the graft can be composed of Wharton's jelly with alternating layers of amnion and chorion. In another aspect, the graft can be composed of Wharton's jelly with a plurality of amnion layers laminated to one another and a plurality of chorion layers laminated to one another.

The actual number of layers present in the grafts will depend upon the surgical need and procedure with which the tissue graft is designed to be used. For example, in dental regenerative procedures such as a root coverage procedure or use in guided tissue regeneration, the thickness of the graft can range from about 0.5 mm to 2 mm. In one aspect, the number of membranes inserted between the Wharton's jelly and the amnion can be one, two, five and or ten, with the ultimate number of layers dependent on the type of graft used, and the expected indication for use.

In one aspect, the graft includes (1) a first membrane of Wharton's jelly; (2) chorion, wherein the chorion includes a chorion stromal layer, wherein the chorion stromal layer is adjacent to the Wharton's jelly; and (3) amnion, wherein the amnion has an exposed basement membrane and an amnion stromal layer, wherein the amnion stromal layer is adjacent to the chorion. In another aspect, the graft includes (1) a first membrane of Wharton's jelly; and (2) amnion, wherein the amnion has an exposed basement membrane and an amnion stromal layer, wherein the amnion stromal layer is adjacent to the Wharton's jelly.

In another aspect, the grafts described herein can be composed of Wharton's jelly where the outer layer of amnion is removed and cut to an approximate length, width, and thickness and a layer of amnion where the epithelium layer has been substantially removed to expose the basement membrane and another biodegradable, biologically compatible material that is sandwiched between the Wharton's jelly and amnion. Examples of such materials include, but are not limited to, allograft pericardium, allograft acellular dermis, amniotic membrane (i.e., both amnion and chorion), umbilical vein, purified xenograft Type-1 collagen, biocellulose polymers or copolymers, biocompatible synthetic polymer or copolymer films, purified small intestinal submucosa, bladder acellular matrix, cadaveric fascia, or any combination thereof.

In one aspect, the tissue graft is dehydrated by chemical dehydration followed by freeze-drying. In one aspect, the chemical dehydration step is performed by contacting the Wharton's jelly, amnion, and or chorion with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue graft is freeze-dried in order to remove any residual water and polar organic solvent. In one aspect, the Wharton's jelly with amnion and/or chorion can be laid on a suitable drying fixture prior to freeze-drying. For example, one or more strips of Wharton's jelly can be laid on a suitable drying fixture, where the gel side is adjacent to the surface of the drying fixture. Next, chorion is laid on top of the Wharton's jelly, stromal side down, followed by layering the amnion stromal side down on top of the chorion such that the exposed basement membrane of the amnion is facing up. In another aspect, the amnion can be placed on the surface of the drying fixture such that the exposed basement membrane is facing down, then chorion is laid on top of the amnion with stromal side up, followed by laying strips of Wharton's jelly on top of the chorion. In another aspect, amnion can be placed on the surface of the drying fixture such that the exposed basement membrane is facing up, then chorion is laid on top of the amnion, followed by strips of Wharton's jelly.

The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Figure 3:
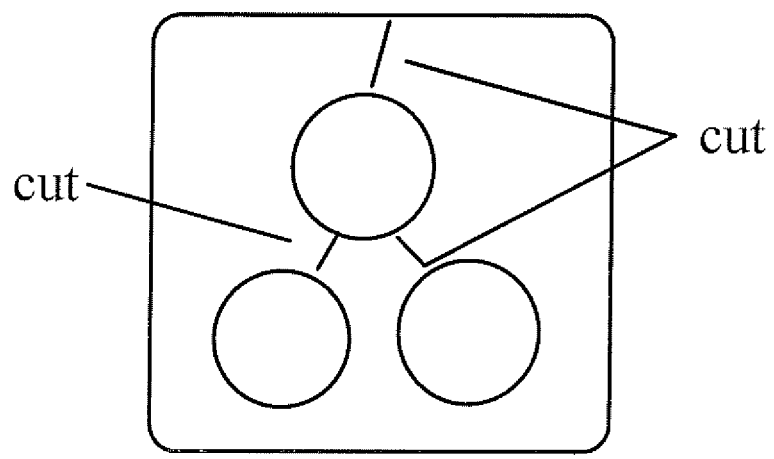
FIG. 3 is a perspective view of an exemplary drying fixture for making the tissue grafts described herein.

In one aspect, similar to that shown in FIG. 3, the receiving surface of the drying fixture 500 has grooves 505 that define the product spaces 510, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another embodiment, instead of having grooves to define the product spaces, the drying fixture has raised ridges or blades.

Within the "empty" space between the grooves or ridges, the drying fixture can include a slightly raised or indented texture in the form of text, logo, name, or similar design 520. This textured text, logo, name, or design can be customized. When dried, the tissue will mold itself around the raised texture or into the indented texture—essentially providing a label within the tissue itself. Preferably, the texture/label can be read or viewed on the tissue graft in only one orientation so that, after drying and cutting, an end user (typically, a clinician) of the dried tissue will be able to tell the stromal side from the basement side of the dried tissue. The reason this is desired is because, during a surgical procedure, it is desirable to place the allograft in place, with amnion basement side down or adjacent the native tissue of the patient receiving the allograft. FIG. 3 illustrates a variety of marks, logos, and text 520 that can be included within the empty spaces 510 of the drying fixture 500. Typically, a single drying fixture will include the same design or text within all of the empty spaces; however, FIG. 3 shows, for illustrative purposes, a wide variety of designs that can be included on such drying fixtures to emboss each graft.

Once the tissue graft composed of Wharton's jelly with chorion and/or amnion is placed on the drying fixture, the drying fixture is placed in the freeze-dryer. The use of the freeze-dryer to dehydrate the tissue grafts can be more efficient and thorough compared to other techniques such as thermal dehydration. In general, it is desirable to avoid ice crystal formation in the placental tissue grafts as this may damage the extracellular matrix in the tissue graft. By chemically dehydrating the placental tissue prior to freeze-drying, this problem can be avoided.

In another aspect, the dehydration step involves applying heat to the tissue graft. In one aspect, the Wharton's jelly with amnion and/or chorion is laid on a suitable drying fixture as discussed above, and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 and 120 minutes. In one aspect, the heating step can be performed at 45 minutes at a temperature of approximately 45 degrees Celcius to dry the tissue sufficiently but without over-drying or burning the tissue graft. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

In certain aspects the tissue graft is not physically altered except for final cutting and packaging (step 180). When completed, the processed tissue graft has a semi-transparent appearance with a whitish coloration. The tissue graft is pliable to withstand bending and sizing in its dry, non-hydrated state. The tissue grafts described herein can be stored at room temperature for extended periods of time.

Cutting & Packaging (Step 180)

Once the graft has been adequately dehydrated, the tissue graft is then ready to be cut into specific product sizes and appropriately packaged for storage, terminal sterilization, and later surgical use. In one aspect, the Tyvek bag containing the dehydrated tissue is placed back into the sterile/controlled environment. The number of grafts to be produced is estimated based on the size and shape of the tissue on the drying fixture(s). An appropriate number of pouches, one for each tissue graft, is then also introduced into the sterile/controlled environment. The drying fixture(s) are then removed from the Tyvek bag.

If the drying fixture has grooves, then the following exemplary procedure can be used for cutting the tissue graft into product sizes. If the drying fixture is configured in a grid pattern, a #20 or similar straight or rolling blade is used to cut along each groove line in parallel. Next, all lines in the perpendicular direction are cut. Alternatively, if the drying fixture has raised edges or blades, then the following procedure can be used for cutting the tissue graft into product sizes. A sterile roller is used to roll across the drying fixture. Sufficient pressure must be applied so that the dehydrated tissue graft is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate tissue graft.

Each tissue graft is then given a final inspection to confirm that there are no tears or holes, that the product size (as cut) is within approximately 1 millimeter (plus or minus) of the specified length and width size and within approximately 250 microns (plus or minus) thick for that particular graft, that there are no noticeable blemishes or discoloration of the tissue graft, and that the textured logo or wording is readable and viewable through the "inner" pouch.

To the extent possible, oxygen is removed from the inner pouch before it is sealed. The inner pouch can be sealed in any suitable manner; however, a heat seal has shown to be effective. In one aspect, after packaging, the product is terminally sterilized by radiation, using gamma or electron beam sterilization with a target dose of 17.5 kGy. Next, each inner pouch is separately packaged in an "outer" pouch for further protection, storage, and shipment.

It should be noted that none of the steps described above involve freezing the tissue graft to kill unwanted cells, to decontaminate the tissue graft, or otherwise to preserve the tissue graft. The dehydrated tissue grafts described herein are designed to be stored and shipped at room or ambient temperature without need for refrigeration or freezing.

Product Release (Step 190)

Before the tissue graft is ready for shipment and release to the end user, all documentation related to the manufacture, recovery and donor eligibility are reviewed and deemed acceptable by the quality assurance department and the medical director.

Appropriate labeling and chain of custody is observed throughout all of the above processes, in accordance with accepted industry standards and practice. Appropriate clean room and sterile working conditions are maintained and used, to the extent possible, throughout the above processes.

II. Applications of Tissue Grafts

The tissue grafts described herein have numerous medical applications. In one aspect, the tissue grafts are composed of Wharton's jelly where the outer layer of amnion is removed and cut to an approximate length, width, and thickness, a layer of chorion, and a layer of amnion where the epithelium layer has been substantially removed. By removing the epithelium layer, cells from the host can more readily interact with the cell-adhesion proteins located onto top and within of the basement membrane of the amnion.

The laminin structure of amnion is nearly identical to that of native human tissue such as, for example, oral mucosa tissue. This includes laminin and laminin-5, found throughout upper portions of the basement membrane. The chorion contains high levels of laminin and laminin-5 throughout the tissue as well.

In one aspect, in the treatment of gingival recession the graft is placed such that the amnion side is placed directly onto the exposed root surface. As discussed above, the high concentrations of laminin-5 found in amnion and chorion facilitate attachment of gingival epithelial direct attachment cells to the surface of the root. In another aspect, when used in guided bone regeneration procedures, the graft is placed such that the amnion side faces outward. The high concentrations of laminin and laminin-5 found in amnion and chorion will in the event primary closure is not obtained or dehiscence exposing the membrane to the oral environment facilitate epithelization and wound closure.

The presence of the Wharton's jelly greatly increases the thickness of the grafts, which provides significant tensile strength useful in a surgical technique called "tunneling." Here, a suture is placed through the graft and pulled underneath the gingival tissue and placed over the exposed root surface and proximal bone in the treatment of gingival recession. Thus, the grafts described herein are useful in applications where it is preferable to secure the graft in place using sutures. The increased thickness makes such grafts more suitable for augmentation procedures aimed at increasing the height and or width of gingival tissue, for use around dental implants or in the treatment of advanced gingival recession defects, where the graft thickness is associated with higher levels of root coverage using surgical techniques such as "vertical incisions," an "envelope flap," a "pouch technique," or "sliding pedicel(s)."

In another aspect, in guided bone regeneration and guided tissue regeneration procedures, the grafts can be placed and tightly adhered over a bone graft, either bone substitute, autogenous bone or a combination of both, proximal walls (e.g., bone, tooth, or a stiff membrane such as a titanium mesh), preventing apical migration of gingival epithelial cells into the protected space. In this aspect, the graft does not require the use of sutures. Additionally, the grafts can be left exposed to the oral environment, reduce the need to release as much gingival tissue to cover the grafted osseous defect, where the exposed areas of the graft are subsequently covered with keratinized tissue following surgery. Moreover, the graft can be used in manner where the graft is placed first, the osseous defect is then filled with graft material, and then folded over and cover the grafted area. The grafts described herein do not induce inflammation. The lack of inflammation reduces post-operative patient pain, graft dehiscence when primary closure is obtained, and osteoclastic resorption of over underlying native bone and graft, which permits better preservation of original osseous dimensions, and natural inflammatory processes associated with resorption the grafts described herein. The large amounts of space between the fibrils in Wharton's jelly and ability to absorb biological fluids, either naturally or man-made, is well suited to naturally facilitate the rate of vascularization by reducing the risk of graft necrosis while increasing the effectiveness of the grafts in the treatment of gingival recession, placed over titanium mesh in vertical and or horizontal bone augmentations, and thicken gingival tissue around implants, guided bone regeneration as well as surgical procedures involving alveolar osseous defects where to goal is to thicken overlaying gingival tissue.

Not wishing to be bound by theory, the grafts composed of Wharton's jelly cut to an approximate length, width, and thickness, a layer of chorion, and a layer of amnion where the epithelium layer has been substantially removed to expose the basement membrane could be highly suitable for use in regenerative procedures due to their superior ability to facilitate cell adhesion and migration, control of cell proliferation and gene expression, maintenance of differentiation phenotypes and stimulation of neurite outgrowth. Their ability to allow for enhanced vascularization as well as their inherent strength and ease of use make the grafts effective in surgical applications involving human mucosa present in the oral cavity, nose, throat, vagina, and rectum.

The grafts described herein can be soaked with a bioactive agent. Examples of bioactive agents useful herein include, but are not limited to, a solution composed of naturally occurring growth factors sourced from platelet concentrates, either using autologous blood collection and separation products, or platelet concentrates sourced from expired banked blood following the methods outlined in U.S. Publication No. 20100222253, which is incorporated herein by reference in its entirety for all purposes. Other examples of bioactive agents include bone marrow aspirate; allograft placentas; stem cells derived from concentrated human placental cord blood stem cells, concentrated amniotic fluid stem cells or stem cells grown in a bioreactor; purified bioactive agents in a suitable buffer solution; or antibiotics. Here, one or more graft layers of the tissue graft can have bioactive agent incorporated in the tissue. Upon application of the wet tissue graft with bioactive agent to the wound, the bioactive agent is delivered to the wound over time.

The tissue grafts are easy to handle and do not readily break. Thus, the use of sutures is not a requirement when using the grafts described herein. However, the tissue grafts may be designed in such a manner to hold sutures or provide specific rates of resorption based on the requirements of the indication in which it is being used.

The tissue grafts described herein have numerous applications and can be used in a variety of procedures. For example, the tissue grafts can be used in the following dental regenerative procedures including the treatment of gingival recession defects, vertical and horizontal gingival augmentation, increasing the amount of attached gingival tissue, elimination of a frenum pull, augment tissue around dental implants, papilla reconstruction, and vestibuloplasty, in guided tissue regeneration over grafted intrabony defects, in guided bone regeneration over grafted extraction sockets, primary and secondary ridge mandibular and maxillary augmentations, and fenestration and dehiscence defects, and in sinus elevation procedures used to cover the lateral window of the sinus and placing over tears in the Schendiarn membrane. In applications involving oral mucosa tissue including treating mouth sores, oral lesions, and replace larger amounts of mucosa tissue lost through disease or traumatic injury.

The tissue grafts can also be used in reconstructive procedures where the tissue is composed of mucosa in the ear, nose, and throat, gynecology, and surgical procedures involving the rectum and anus.

The tissue grafts described herein can include one or more bone grafts and/or regenerative materials. Bone grafts are a tissue or material used to repair a defect or deficiency in osseous tissue. Bone grafts generally fall into four categories: autografts, which are obtained from the patient, and allografts, xenografts and alloplasts. Bone grafts generally possess one or more of the following characteristics: (1) ostegenic potential—the presence of viable cells; (2) osteoinductive—contains noncollagenous proteins that attract cells, induce bone formation, and or hasten cell migration; and (3) osteoconductive—serves as scaffold for cellular migration and provides calcium phosphate.

Autograft bone harvested from the iliac crest, rib, chin, or intraoral cancellous bone from the maxillary tuberosity or extraction sites, possesses osteogenic, osteoinductive, and osteoconductive properties. Allograft materials refer to tissue derived from human cadavers, and include iliac cancellous bone and marrow, freeze-dried cortical and cancellous bone, and demineralized freeze-dried cortical and cancellous bone. Caderivic allografts possess osteoconductive and osteoinductive properties. Xenografts are derived from non-human species. These graft materials only possess osteoconductive properties as all or most of the proteinaceous material is removed leaving behind an inert absorbable hydroxapapatite scaffolding. Alloplasts are synthetically manufactured and include non-porous hydroxyapatite, porous hydroxyapatite, tri-calcium phosphate, bioactive glass, fluoroapatite, carbonated apatite, calcium sulfate, calcium carbonate, and combinations thereof, and provide varying degrees of osteoconductive properties.

In other aspects, the grafts described herein can be wrapped around meshes or porous devices in craniofacial surgery including the treatment of grafted bony defects caused from trauma, surgically created bone defects (e.g., burrholes and trephine defects, zygomatic defects, and orbital defects), and in orthopedic surgery in open and closed fractures, segmental defects, osteochondral defects, spinal fusion, and other non-load bearing regeneration procedures.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts described herein can be used to wrap tendon repairs to prevent scar formation on the healing tendon. They can also provide a protective, enclosed environment for the repair to progress successfully. The tissue grafts can be used as an off-the-shelf tendon and ligament to replace the need to purchase an allograft or perform tendon or ligament transfer.

In other aspects, the tissue grafts described herein can be used in the reinforcement of rotator cuffs. Some rotator cuff tears are large enough that they require a reinforcement matrix to support the repair due to lack of viable native tissue. The tissue grafts described herein can be used as a matrix to reinforce a repair. In one aspect, the tissue grafts described herein can be used to repair knee cartilage. For example, the tissue grafts can be used as a barrier to hold cell cultured chondrocytes or other pro-cartilage regeneration matrix inside a chondral defect. In this aspect, the tissue graft would be utilized as a flap to close the defect and hold the matrix in place.

In one aspect, the tissue grafts can be used to repair peripheral nerves. The tissue graft can be used as a wrap on nerve repairs to prevent scar formation onto the healing nerve. The tissue graft can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts can be laid on the nerves to keep them from scarring and possibly damaging the nerves.

In other aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In one aspect, the grafts described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the grafts described herein can function as a tissue regeneration template that delivers essential wound healing factors, extracellular matrix proteins and inflammatory mediators to help reduce inflammation, enhance healing, and reduces scar tissue formation.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the graft protects the spinal dura from post-surgical trauma from the surrounding surgical site. For example, the grafts can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue graft can be applied directly to the spinal dura, the surrounding region of the spine to include nerve roots, or a combination thereof. Due to the unique structure of vertebrae, the tissue graft can be cut into any shape or dimension so that it can be placed and affixed at the appropriate position in the subject. For example, when the tissue graft is used for bi-lateral coverage, membranes in the shape of a rectangle allow the tissue graft to fit around the posterior spinal process, which minimizes lateral movement. In addition to minimizing lateral movement, the tissue graft can also provide proximal and distal barrier coverage where the spinal lamina has been removed for exposure to the affected area. In one aspect, to ensure proper placement, the graft can be embossed on the exposed basement membrane of the graft to ensure proper placement of the graft in the subject. In particular, proper graft placement will ensure that the basement membrane of the graft is in direct contact with the spinal dura or surrounding region. For example, proper membrane placement and orientation is important when applying the material in spinal applications where a posterior or anterior approach is utilized.

The grafts are useful in preventing or reducing scar formation that can result from a variety of surgical procedures associated with the spine. The grafts can be used after any procedure in the neck, mid-back, or lower back. Depending upon the application, the epithelium of the amnion membrane can be substantially removed. For example, in posterior procedures such as a laminectomy or discectomy, the epithelium layer is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures. Thus, the grafts described herein provide an unmet need in these procedures.

In other aspects, the epithelial cell layer is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the grafts provide additional protection to the vertebral surgical site by maintaining separation from the peritoneum, larger vessels, and abdominal musculature. The membrane serves as a reduced friction anatomical barrier against adhesions and scaring. For example, the grafts can prevent scar tissue binding major blood vessels to the spine. This is a common problem with post-spinal surgery, which requires a second surgical procedure to address this.

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue graft can be used as an anti-adhesion barrier after removal of ovarian cyst or aid in the repair of vaginal wall erosion.

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels).

The tissue grafts described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the tissue grafts can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

Depending upon the application of the graft, the graft can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

Although the tissue grafts described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

In one aspect, the following process is used to make a tissue grafts described herein:

(a) obtaining a placenta from a subject, wherein the placenta comprises an amniotic sac and an umbilical cord;

(b) separating the amniotic sac into a layer of amnion and chorion tissue, wherein the amnion comprises epithelium cells adjacent to a basement membrane;

(d) removing substantially all of the epithelium cells to expose the basement membrane of the amnion;

(e) separating the Wharton's jelly from the umbilical cord vascular components (f) cutting off the outer layer of amnion from the Wharton's jelly;

(g) cutting the Wharton's jelly to pre-determined length, width and thickness;

(h) mounting the Wharton's jelly onto a surface of a drying fixture;

(i) layering chorion on top of the Wharton's jelly (j) layering amnion on top of the chorion;

(i) dehydrating the layered tissue graft on the drying fixture; and (k) cutting strips of dehydrated amnion-chorion-Wharton's jelly from surrounding chorion and amnion.

Preparation of Wharton Jelly's a. Materials and Equipment

The following items were sterilized, where appropriate, or purchased sterile and used to process the placenta: stainless steel basin, drape, 32 oz. bowl, processing tray, cleaning kit (ruler, scissors, forceps and small curved forceps), transfer kit (scissors and forceps), rocker (Barnstead Lab Line, Model 2314), antibiotic solution (0.2% Streptomycin sulfate and 0.015% Gentamicin sulfate), water, 18% NaCl, 4×4 cm gauze, Nalgene jars, Isosorb, ruler, and mosquito scissors. A human placenta, less than 21 days old at the start of processing, was obtained from a local hospital. All solutions, disposables, instruments and containers used in the biological safety cabinet were sterile.

b. Procedure

A sterile field was prepared in a disinfected biological safety cabinet. Two drapes were laid to cover the bottom of the work tray and the bowl, cleaning kit, gauze, mosquito scissors and Nalgene jars were aseptically moved to the work tray. The placenta was removed from the recovery transport container, ascetically placed in the stainless steel basin, and the basin transferred to the field. Hyperisotonic saline (18% NaCl) was poured into the bowl and into the Nalgene container.

The tissue was assessed for any discoloration, debris, an unacceptable odor and signs of damage. Information was recorded and any damage diagramed. As the tissue was acceptable, the operator proceeded.

Starting at the umbilical cord, the amnion was gently lifted away from the chorionic disk to separate the chorion from the amnion The bulk of the amnion was carefully removed and the remaining amnion and chorion cut from the disk. Extraneous and irregular edges were trimmed and clots removed using gauze. The amnion and chorion were separated from one another. The amnion and chorion were subsequently rinsed in 18% hypertonic saline for 10 minutes to loosen remaining clots.

The umbilical cord was cut away from the chorionic disk. The veins and artery were located at the end of the cord. The cord was cut through one of the vessels to the outer membrane along the longitudinal axis of the cord and between the vessels, as shown in FIG. 2. The mosquito scissors were used to trim any vein and artery walls that were visible.

The Wharton's jelly was placed in a Nalgene jar filled at room temperature with 18% NaCl, aseptically covered with a lid to seal, removed from the hood, labeled, transferred to a rocker platform and agitated at ambient temperature for 60 minutes. During the incubation, the hood was cleaned and a sterile work area set up with the following materials: Nalgene jar filled with prewarmed 18% NaCl, one sterile drape and one transfer kit.

At the end of the 60 minutes, the Nalgene jar containing the Wharton's jelly was disinfected and aseptically transferred back to the work area. The Wharton's jelly was aseptically removed from the jar with forceps and placed on the drape. Any visible vein and artery walls were cut away with mosquito scissors, making sure not to cut the cord below 1.25 mm in thickness. A clean Nalgene container was filled with 500 ml warm (48° C.) 18% NaCl. The Wharton's jelly was transferred to the clean Nalgene jar with fresh, warm 18% NaCl and the lid secured tightly. The jar was placed on the rocker platform and agitated for 70 minutes. During incubation, the used disposables in the hood were discarded and the area disinfected. Following the incubation period, the Nalgene jar was removed from the shaker, the outside of the Nalgene jar disinfected, and returned to the hood.

The decontamination step was next performed. The Wharton's jelly was placed in a Nalgene jar filled with premixed antibiotics ((0.2% Streptomycin sulfate and 0.015% Gentamicin sulfate), aseptically covered with a lid, removed from the hood, labeled, transferred to a rocker platform and agitated at ambient temperature for 60 minutes. The Nalgene jar was placed at 1-10° C. for 16 hours.

The hood was disinfected and a sterile work area established containing the following materials: work tray, Nalgene jar filled with sterile water, one sterile drape, sterile bowl containing sterile water and one transfer kit. The jar containing the tissue was opened and the umbilical cord removed from the antibiotic solution with forceps and placed in the bowl of sterile water. The Wharton's jelly was rinsed in a basin with water for 1-2 minutes and transferred to the Nalgene with sterile water. The lid was tightly secured on the Nalgene. The Nalgene was removed from the hood and placed on the rocker platform for 60 minutes. The hood was cleaned and disinfected. A work area in the hood was set up containing: a sterile bowl filled with sterile water, dehydration kit (scissors, forceps and small curved forceps), mosquito scissors, ruler, drying board, drying rack and clamps. After the incubation, the outside of the Nalgene jar containing the tissue was disinfected and returned to the hood.

The tissue was aseptically removed from the jar and transferred to a sterile bowl. The thickness of the tissue was measured (1.25 mm+/−0.25 mm.) to ensure the desired thickness was achieved.

Preparation of Amnion a. Materials and Equipment

The following items were sterilized, where appropriate, or purchased sterile and used to process the placenta: stainless steel basin, drape, 32 oz. bowl, processing tray, cleaning kit (ruler, scissors, forceps and small curved forceps), transfer kit (scissors and forceps), rocker (Barnstead Lab Line, Model 2314), antibiotics (0.2% Streptomycin and 0.015% Gentamicin), water, 18% NaCl, 4×4 cm gauze, Nalgene jars, Isosorb, ruler, a mosquito scissors. A human placenta, less than 21 days old at the start of processing, was obtained from a local hospital. All solutions, disposables, instruments and containers used in the biological safety cabinet were sterile.

b. Procedure

A sterile field was prepared in a disinfected biological safety cabinet. Two drapes were laid to cover the bottom of the work tray and the bowl, cleaning kit, gauze, mosquito scissors and Nalgene jars were aseptically moved to the work tray. The placenta was removed from the recovery transport container, placed in the stainless steel basin, and the basin transferred to the field. Hyperisotonic saline (18% NaCl) was poured into the bowl and into the Nalgene container.

The placenta was assessed for any discoloration, debris, an unacceptable odor and signs of damage. A rough measurement of length and width of the amnion was taken (amnion: 30 cm×40 cm). Information was recorded and any damage diagramed. As the tissue was acceptable, the operator proceeded.

Starting at the umbilical cord, the amnion was gently lifted away from the chorionic disk to separate the chorion from the amnion. The bulk of the amnion was carefully separated from the chorion by blunt dissection and the remaining amnion and chorion cut from the disk. Extraneous and irregular edges were trimmed and clots removed using gauze. The amnion was placed on the tray with the epithelial side up and the epithelial layer of cells was removed by gently scraping the amnion with a cell scraper. The amnion was rinsed in 18% hyperisotonic saline in the basin for 10 minutes to loosen remaining clots.

The tissue was transferred to the Nalgene container with saline, the lid tightened, and the Nalgene was agitated on a rocker for 60 minutes. The Nalgene container was returned to a clean sterile field in the biological safety cabinet and the container opened. The amnion was transferred to a Nalgene container with antibiotic solution, the lid tightened and the container agitated on a rocker for 90 minutes. Following the incubation, the amnion was refrigerated at 1-10° C. for 18 hours and 25 minutes.

The tissue was transferred into a Nalgene containing sterile water, the lid closed, and the tissue agitated on a rocker for 60 minutes. Following the incubation, the tissue was ready for the preparation of the graft.

Preparation of Chorion

After the amnion and chorion have been separated and blood clots have been removed, the chorion was placed into an initial rinse of 18% saline solution for 30-60 minutes. At the completion of the initial rinse, the chorion was placed into a new sterile container and 18% saline solution heated to 48° C. was decanted into container. The container was sealed. The container was placed on rocker plate and agitated for 60-90 minutes. After the 60-90 minute agitation was complete, the chorion was removed and placed into a new separate sterile container. 18% saline solution heated to 48° C. was decanted into the container. This step is optional, and can be used if residual blood is still visible on tissue since this step provides additional cleaning. At the completion of the second 60-90 minute agitation cycle, the chorion was removed and placed into antibiotic solution and agitated for 60-90 minutes. Following the antibiotic agitation, tissue processing may be interrupted and the tissue held at 1-10° C. for no longer than 24 hours. Thereafter, processing resumed accordingly. Once the antibiotic wash was complete, the chorion was removed and placed into sterile water and agitated for 30-60 minutes.

Preparation of the Amnion-Chorion-Wharton's Jelly Graft

A sterile field was prepared in the biological safety cabinet and the sterile non-reversed embossed drying board was placed in the field. The Wharton's jelly was laid gel side down in direct contact with the drying fixture. A single layer of chorion was then placed laid stromal side done on top of the Wharton's jelly. Air bubbles were removed. A single layer of amnion was then placed on the stromal layer down, on top of the chorion. Air bubbles were removed. The drying rack was placed on top of the amnion-chorion-Wharton jelly graft and the drying rack and drying board were clamped together. The clamped fixture was then placed in the pre-sterilized drying oven set at 45° C. and incubated until completely dry (21 hours).

Preparation of Individual Amnion-Chorion-Wharton's Jelly Grafts

The hood was disinfected and a sterile work set up containing the following materials: sterile drapes, cutting board, cutting kit (2 rulers, scissors, forceps, small curved forceps, knife holder, needle holder, and micro spatula), scalpel blade, and inner foil pouches. The tissue was removed from the dried fixture and aseptically transferred into the work area. A ruler and scalpel was used to cut grafts into desired sizes (1.0×1.3 cm, 1.0×2.5 cm, 1.0×3.5 cm). Each graft was placed into its own inner foil pouch so that the embossment is read left to right. Once all grafts were cut and placed into pouches, the inner pouches were sealed and labeled with tissue identification numbers.

In Vivo Studies a. Amnion/Wharton's Jelly Graft

Soft Tissue Graft—Gingival Recession

Figure 4:
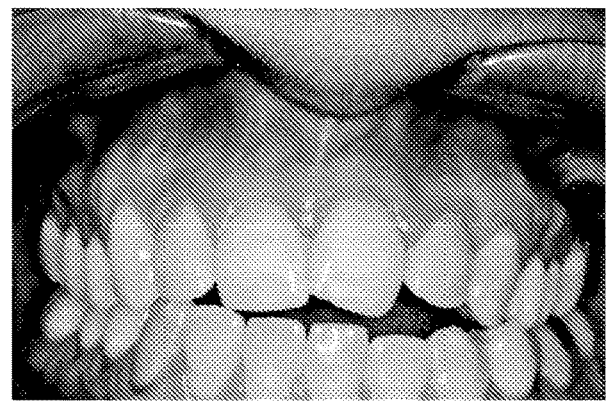
FIG. 4 shows the use of an amnion/Wharton's jelly graft as a soft tissue substitute for gingival recession.
Figure 4:
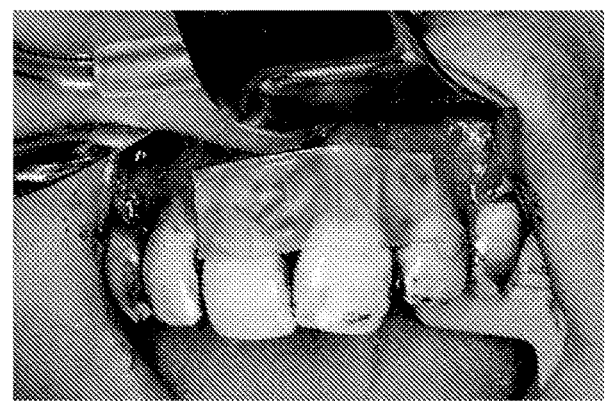
Figure 4:
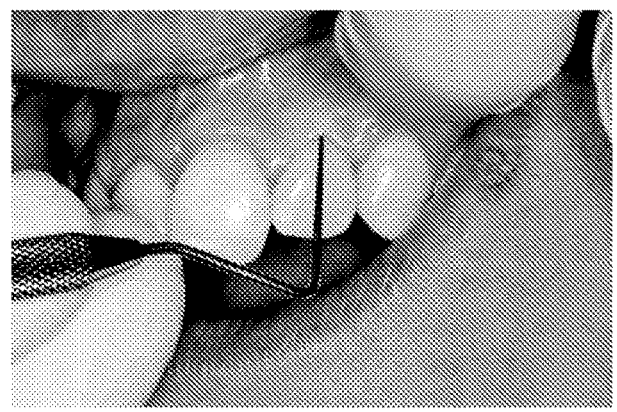

FIG. 4A shows a 2 mm defect tooth #8 and 1 mm defect on tooth #8. After scaling and root planning, the root surfaces were detoxified using tetracycline and Emdogain was applied to the root surfaces. The amnion/Wharton's jelly graft was then placed over the defects and proximal bone (FIG. 4B). No sutures were used to secure the graft in place. The flap was advanced fully covering the graft. At 9 weeks, 100% root coverage and some increase in tissue thickness (FIG. 4C).

Barrier Membrane—Site Preservation

Figure 5:
FIG. 5 shows the use of an amnion/Wharton's jelly graft as a barrier membrane at an extraction site for site preservation.
Figure 5:
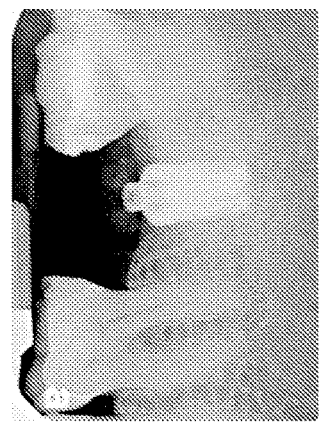
Figure 5:
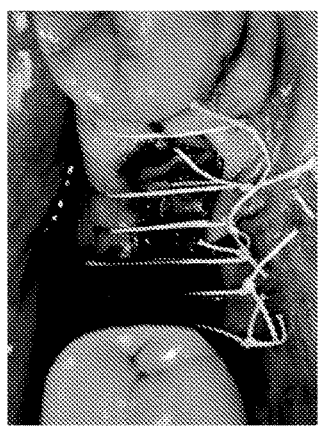
Figure 5:
Figure 5:
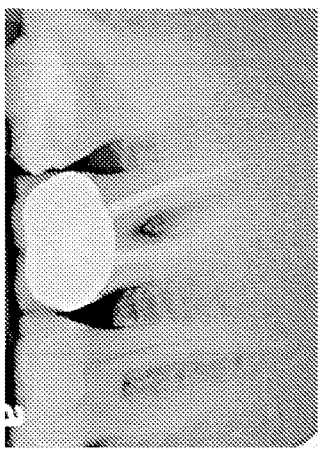
Figure 5:

Tooth #31 was atraumatically extracted. The extraction site was grafted with freeze dried bone allograft and covered with the amnion/Wharton's jelly graft. Primary closure was not obtained. At 10 day post-op, inward migration of gingival tissue over the surgical site and granulation tissue covering the exposed of portions of the membrane was observed (FIG. 5C). At 2.5 months, the site was completely covered with keratinized tissue (FIG. 5D), and there was excellent new bone formation (FIG. 5E). FIG. 5F shows that implant was successfully placed.

b. Amnion/Chorion/Wharton's Jelly Graft

Soft Tissue Substitute—Gingival Recession

Figure 6:
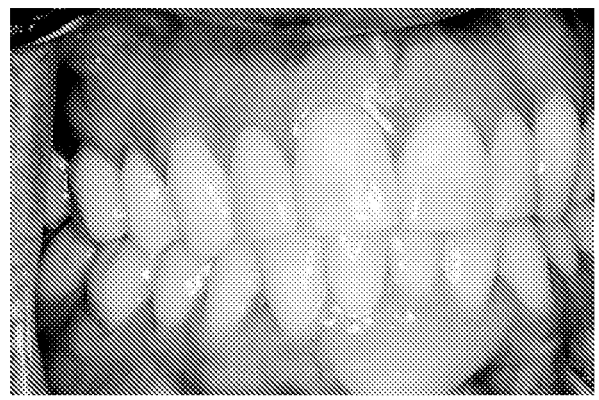
FIG. 6 shows the use of an amnion/chorion/Wharton's jelly graft as a soft tissue substitute for gingival recession.
Figure 6:
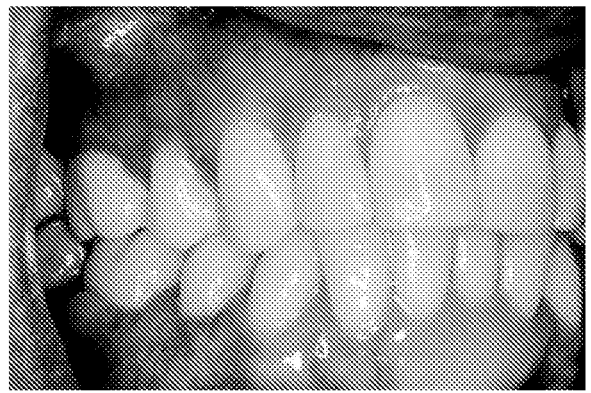
Figure 6:

FIG. 6A shows a 2 mm defect tooth #3, 3 mm defect on tooth #4, 2 mm defect on tooth #29, and 3 mm defect on tooth #30. The defects in the mandible were treated with connective tissue graft (CTG) and the defects in maxilla with the amnion/chorion/Wharton's jelly graft. Both CTG and the graft were sutured into place and completely covered by the overlaying flap. At two week all treated sites showed minimal inflammation and excellent healing (FIG. 6B). At three months, all treated sites had 100% root coverage, an increase in tissue thickness, and excellent esthetic outcome (FIG. 6C).

Barrier Membrane—Site Preservation

Figure 7:
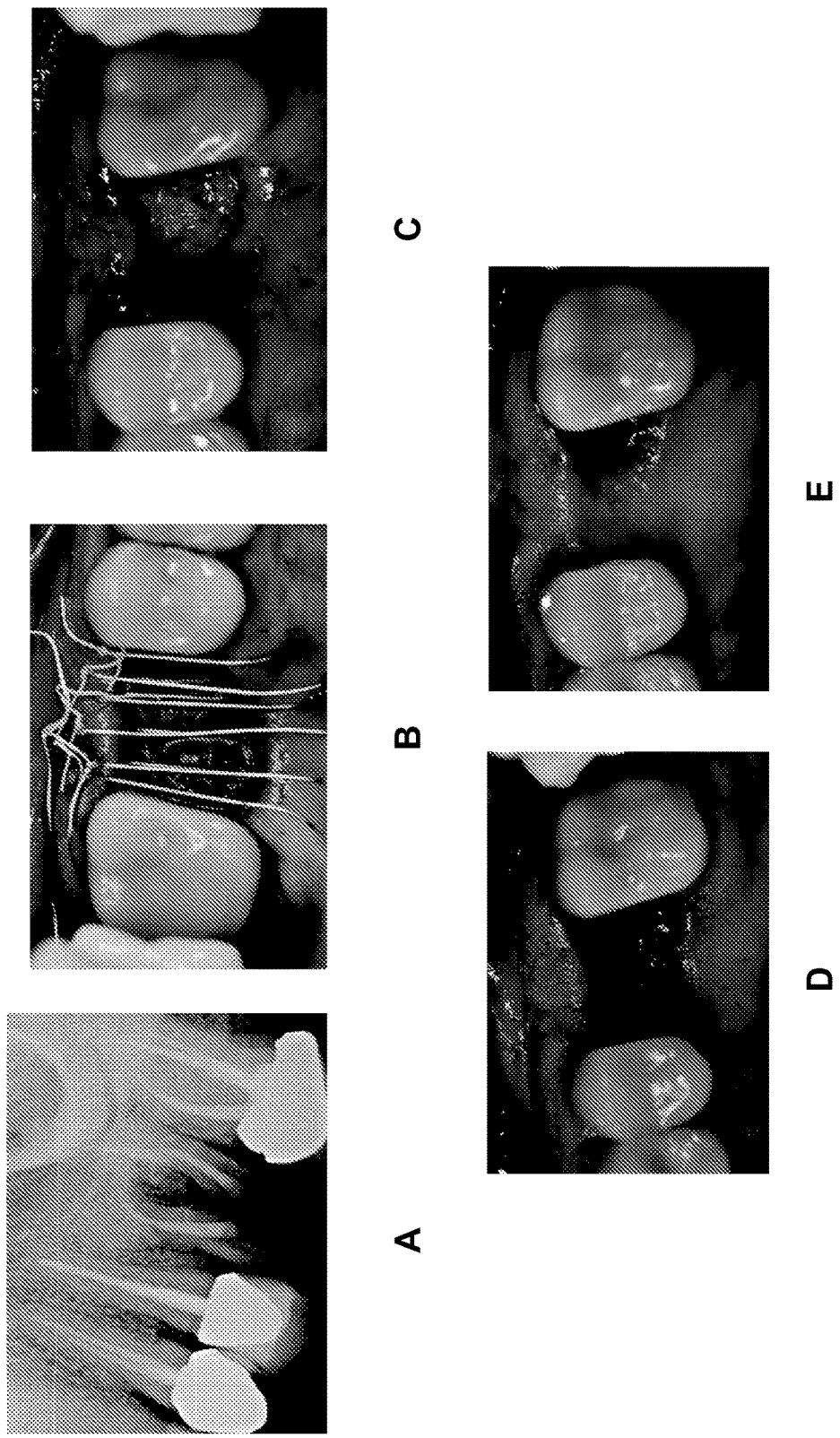
FIG. 7 shows the use of an amnion/chorion/Wharton's jelly graft as a barrier membrane at an extraction site for site preservation.

Tooth #14 was atraumatically extracted (FIG. 7A). The extraction site was grafted with freeze dried bone allograft and covered with the amnion/Wharton's jelly graft (FIG. 7B). Primary closure was not obtained. At 2 weeks post-op, inward migration of gingival tissue and granulation tissue covering the exposed of portions of the membrane was observed (FIG. 7C). At 4 weeks, complete coverage of the exposed graft was observed (FIG. 7D). At 8 weeks, almost complete keratinization of gingival tissue was observed (FIG. 7E). Note the tissue is thicker compared to the amnion/Wharton's jelly graft.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplar.

The invention claimed is:

1. A tissue graft comprising a first layer, a second layer, and a third layer laminated together, said first layer comprising a placental amnion, said second layer comprising a chorion, and said third layer comprising Wharton's jelly,
   wherein the amnion comprises an exposed basement membrane and an amnion stromal layer, wherein the amnion stromal layer is adjacent to the chorion, and wherein the chorion comprises a chorion stromal layer, wherein the chorion stromal layer is adjacent to the Wharton's jelly,
   wherein an intermediate layer of said amnion has not been substantially removed.

2. The graft of claim 1, wherein the graft is substantially dry prior to use.

3. The graft of claim 2 which has been hydrated.

4. The graft of claim 1, wherein the graft is hydrated with an aqueous solution comprising naturally occurring growth factors sourced from platelet concentrates, either using autologous blood collection and separation products, or xenograft sources that comprise fetal swine teeth and blood concentrates, purified natural bioactive agents, recombinant biological modifiers that comprise recombinant platelet derived growth factor and recombinant fibroblast growth factor, or any combination thereof.

5. The graft of claim 1, wherein the graft is about 1 mm in thickness.

6. The graft of claim 1, wherein the graft comprises laminin and laminin-5.

7. The graft of claim 1, wherein the graft is soaked in platelet concentrates prior to use, said platelet concentrates sourced from expired banked blood.

8. The graft of claim 1, wherein the graft is soaked with a bioactive agent comprising naturally occurring growth factors sourced from platelet concentrates, using autologous blood collection and separation products; bioactive agents sourced from allograft placentas; bone marrow aspirate; a solution of purified natural bioactive agents, recombinant bioactive agents, or any combination thereof.

9. The graft of claim 1, wherein the amnion and chorion are obtained from a mammal other than a human.

10. A method for facilitating vascularization of a wound and promoting wound healing, the method comprising contacting the wound site with the graft of claim 1.

11. A method for facilitating cell migration of gingival epithelia cells and promoting attachment of gingival epithelia cells to a tooth root, the method comprising contacting the gingival epithelia cells with the graft of claim 1.

12. A method for promoting wound healing associated with a dental surgical procedure, comprising contacting the wound with the graft of claim 1.

13. A method for preventing or reducing scar formation on or near the spine after a surgical procedure, the method comprising applying to a subject the tissue graft of claim 1 directly to the spinal dura of the subject or a region near the spine.

14. A method for treating a dural tear in a subject, the method comprising applying directly to the dural tear the tissue graft of claim 1.

15. A method for promoting wound healing associated with an orthopedic application, associated with an ENT application, involving a subject's extremities, associated with an ophthalmological application, associated with a gynecological application, associated with an urological application, or associated with general surgery, wherein the method comprises contacting the wound with the graft of claim 1.

16. A method for promoting wound healing in the human mucosa in the oral cavity, nose, throat, vagina, or rectum, the method comprising contacting the wound site with the graft of claim 1.

17. A method for promoting the healing of a wound in a subject, the method comprising applying to the wound the graft of claim 1, wherein the wound is in the cranial dura, a wound resulting from a perioplastic procedure, a frenum pull, in a patella, in a Schneiderian membrane in the sinus cavity, or is in soft tissue around a dental implant.

18. A method for preventing or reducing scar formation on or near a wound, the method comprising applying to the wound the graft of claim 1.

* * * * *